United States Patent
Lange

(10) Patent No.: US 7,351,980 B2
(45) Date of Patent: Apr. 1, 2008

(54) ALL-REFLECTIVE OPTICAL SYSTEMS FOR BROADBAND WAFER INSPECTION

(75) Inventor: Steven R. Lange, Alamo, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 90 days.

(21) Appl. No.: 11/097,526

(22) Filed: Mar. 31, 2005

(65) Prior Publication Data

US 2006/0219930 A1 Oct. 5, 2006

(51) Int. Cl.
*G01N 21/33* (2006.01)
(52) U.S. Cl. .................................. 250/372
(58) Field of Classification Search ............ 250/372
See application file for complete search history.

(56) References Cited

U.S. PATENT DOCUMENTS

| | | | |
|---|---|---|---|
| 4,934,805 A * | 6/1990 | Pinson | 359/694 |
| 5,559,338 A | 9/1996 | Elliott et al. | |
| 5,917,594 A | 6/1999 | Norton | |
| 5,999,310 A | 12/1999 | Shafer et al. | |
| 6,483,638 B1 | 11/2002 | Shafer et al. | |
| 6,560,039 B1 | 5/2003 | Webb et al. | |
| 6,570,650 B1 | 5/2003 | Guan et al. | |
| 6,603,541 B2 | 8/2003 | Lange | |
| 2004/0012774 A1 | 1/2004 | Lange | |
| 2005/0006590 A1 * | 1/2005 | Harrison | 250/372 |
| 2005/0280906 A1 * | 12/2005 | Scheiner et al. | 359/726 |
| 2006/0018011 A9 * | 1/2006 | Wilklow | 359/359 |
| 2006/0083470 A1 * | 4/2006 | Solarz | 385/125 |

FOREIGN PATENT DOCUMENTS

| EP | 1306698 A1 | 5/2003 |
|---|---|---|
| EP | 1333323 A2 | 8/2003 |

OTHER PUBLICATIONS

International Search Report, PCT/US2006/010042, mailed Jul. 7, 2006, not a publication.

* cited by examiner

*Primary Examiner*—Constantine Hannaher
(74) *Attorney, Agent, or Firm*—Baker & McKenzie LLP

(57) ABSTRACT

All-reflective optical systems for broadband wafer inspection are provided. One system configured to inspect a wafer includes an optical subsystem. All light-directing components of the optical subsystem are reflective optical components except for one or more refractive optical components, which are located only in substantially collimated space. The refractive optical component(s) may include, for example, a refractive beamsplitter element that can be used to separate illumination and collection pupils. The optical subsystem may also include one or more reflective optical components located in substantially collimated space. The optical subsystem is configured for inspection of the wafer across a waveband of greater than 20 nm. In some embodiments, the optical subsystem is configured for inspection of the wafer at wavelengths less than and greater than 200 nm.

27 Claims, 3 Drawing Sheets

ALL-REFLECTIVE OPTICAL SYSTEMS FOR BROADBAND WAFER INSPECTION

BACKGROUND OF THE INVENTION

1. Field of the Invention

This invention generally relates to all-reflective optical systems for broadband wafer inspection. Certain embodiments relate to a system that includes an optical subsystem of which all light-directing optical components are reflective optical components except for one or more refractive optical components that are located in substantially collimated space such that the refractive optical component(s) do not introduce aberrations to the light. The reflective optical components are located in non-collimated space and substantially collimated space.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

One obvious way to improve the detection of relatively small defects is to increase the resolution of an optical inspection system. One way to increase the resolution of an optical inspection system is to decrease the wavelength at which the system can operate. As the wavelength of inspection systems decrease below the visible waveband, relatively good resolution can be easily achieved for relatively small wavebands. For example, optical components that have relatively low aberrations across small wavebands are relatively easy to design and fabricate.

However, it is also desirable for inspection systems to be able to operate over a relatively broad waveband such that defect detection can be performed across a broad range of wavelengths or a number of smaller bandwidths selectable from a larger bandwidth for a given circumstance. Having the capability to generate inspection data across a broad waveband has obvious benefits such as increasing the flexibility of the inspection system for performing inspection of a wide variety of wafers that have substantially different characteristics. In addition, inspection data generated across a broad waveband may provide significantly more information about a wafer than inspection data generated at only a single wavelength or across a narrow waveband. Furthermore, thin-film interference between transparent layers on a semiconductor wafer can create measurement noise because of variations in the thickness of the layers. If a broadband light source is used to illuminate the wafer, the interference between the different wavelengths tends to balance out thereby minimizing the interference noise effect. Thus, having a broadband illumination source is desirable to minimize noise thereby allowing smaller defects to be seen.

Designing a broadband inspection system that can operate at wavelengths below the visible waveband is not a trivial matter. However, some optical inspection systems have been designed for broadband wafer inspection below the visible waveband using only refractive lenses, refractive lenses formed of a combination of both fused silica and calcium fluoride ($CaF_2$) elements, or catadioptric lens assemblies that include a mixture of both fused silica and $CaF_2$ elements. Fused silica in combination with a material such as $CaF_2$ or a mirror/lens arrangement that includes elements formed of such a combination of materials are used in inspection system lenses to overcome the dispersion of light by fused silica thereby making an inspection system having a significant bandwidth possible.

The material combinations described above, however, typically cannot be used for a broadband optical system designed to operate at wavelengths below 230 nm. For example, the transmission of fused silica drops dramatically below about 185 nm due to absorption of the light by the oxygen ($O_2$) molecules in the fused silica. Therefore, the transmission properties of fused silica prohibit any broadband solution below that wavelength as there are not two dissimilar refractive materials available for use below that wavelength. Even above that wavelength, the dispersion of fused silica becomes relatively large at wavelengths approaching the absorption edge (See FIG. 2). Therefore, the achievable waveband below about 230 nm is rather narrow using a lens that includes fused silica elements. For example, typically a waveband of only 10 nm to 20 nm in the wavelength range around 200 nm is achievable using inspection systems that include fused silica elements in combination with $CaF_2$ in a catadioptric configuration. When the dispersion of fused silica flattens out at longer wavelengths, then a longer waveband is feasible.

Examples of lenses that include fused silica elements and are configured for microscopic inspection across a waveband from 230 nm to 370 nm are illustrated in U.S. Pat. No. 5,999,310 to Shafer et al., which is incorporated by reference as if fully set forth herein. The lenses described in this patent provide significant wafer inspection capability as well as advantages such as the ability to use different types of illumination and minimization of aberrations such as coma, astigmatism, primary color aberrations, and residual lateral color aberrations. Therefore, although significant utility in wafer inspection applications has been found for these lenses, due to the transmission properties of fused silica described above, these lenses are not suited for broadband wafer inspection below wavelengths of 200 nm or even 230 nm. These limitations are not specific to the lenses described in this patent but will be true for any inspection system that includes at least one lens element that is formed of fused silica.

Accordingly, it would be advantageous to develop a wafer inspection system that provides wafer inspection capability across a broad waveband that includes wavelengths below and above 200 nm.

SUMMARY OF THE INVENTION

The following description of various embodiments of systems configured to inspect a wafer and methods for inspecting a wafer is not to be construed in any way as limiting the subject matter of the appended claims.

One embodiment relates to a system configured to inspect a wafer that includes an optical subsystem. All light-directing optical components of the optical subsystem are reflective optical components except for one or more refractive optical components located only in substantially collimated space. The optical subsystem is configured for inspection of the wafer across a waveband of greater than 20 nm.

In one embodiment, the waveband includes wavelengths below about 200 nm. In another embodiment, the waveband is selected based on characteristics of the wafer. In some embodiments, the waveband is selected to include wavelengths at which materials on the wafer are both opaque and transparent. In yet another embodiment, the waveband is selected to increase the signal-to-noise ratio corresponding to a defect on the wafer. In additional embodiments, the waveband includes wavelengths in a range from about 150 nm to about 450 nm.

In one embodiment, the optical subsystem includes one or more light sources. In one embodiment, the one or more light sources include one or more fiber lasers. In another embodiment, the one or more light sources include a laser configure to generate light at multiple harmonics. In one such embodiment, the optical subsystem is configured to direct light at one of the multiple harmonics to the wafer, light at a plurality of the multiple harmonics to the wafer sequentially, or light at a plurality of the multiple harmonics to the wafer simultaneously. In a different embodiment, the one or more light sources include a cascade arc. In other embodiments, the one or more light sources include an arc lamp, a laser, a laser configured to generate light at multiple harmonics, or some combination thereof.

In another embodiment, the reflective optical components include two or more optical components that are configured to alter a magnification of light collected by the optical subsystem. In some embodiments, the optical subsystem is configured to have a magnification from about 50× to about 500×.

In an embodiment, the optical subsystem is configured to have a low central obscuration. In an additional embodiment, the optical subsystem is configured to have an accessible pupil separated in illumination and collection paths by a beamsplitter. In another embodiment, the optical subsystem is configured to have an accessible Fourier plane.

In some embodiments, the one or more refractive optical components include a refractive beamsplitter element located in the substantially collimated space. In one such embodiment, the refractive beamsplitter element is formed of calcium fluoride. In another such embodiment, the refractive beamsplitter element is formed of fused silica, and the waveband of the optical subsystem includes wavelengths greater than about 190 nm.

In some embodiments, a numerical aperture on the object side of the optical subsystem is greater than about 0.70. In another embodiment, a numerical aperture on the object side of the optical subsystem is greater than or equal to about 0.90. In an additional embodiment, a field of view of the optical subsystem is greater than about 0.1 mm. In addition, the field of view of the optical subsystem may be greater than or equal to about 0.8 mm. In a further embodiment, the optical subsystem is substantially telecentric in object space. In another embodiment, the optical subsystem is low in distortion. Each of the embodiments of the system described above may be further configured as described herein.

A different embodiment relates to another system configured to inspect a wafer. This system includes a broadband optical subsystem. All light-directing optical components of the broadband optical subsystem are reflective optical components except for one or more refractive optical components only located in substantially collimated space. The broadband optical subsystem is configured for inspection of the wafer at wavelengths both less than and greater than 200 nm. This system may be further configured as described herein.

An additional embodiment relates to a method for inspecting a wafer. The method includes directing light from a light source to the wafer through non-collimated space using only reflective optical components. The light has a waveband of greater than 20 nm. The method also includes directing light from the wafer to a detector through non-collimated space using only reflective optical components. In addition, the method includes detecting defects on the wafer using signals generated by the detector.

In one embodiment, the light from the light source has one or more discrete wavelengths. In one such embodiment, directing the light from the light source to the wafer includes directing light having a single of the one or more discrete wavelengths to the wafer. In a different such embodiment, directing the light from the light source to the wafer includes directing light having a combination of the one or more discrete wavelengths simultaneously to the wafer. Each of the one or more discrete wavelengths may alternatively be directed from the light source to the wafer sequentially. Each of the embodiments of the method described above may include any other step(s) described herein.

BRIEF DESCRIPTION OF THE DRAWINGS

Other objects and advantages of the invention will become apparent upon reading the following detailed description and upon reference to the accompanying drawings in which.

Figure 1:
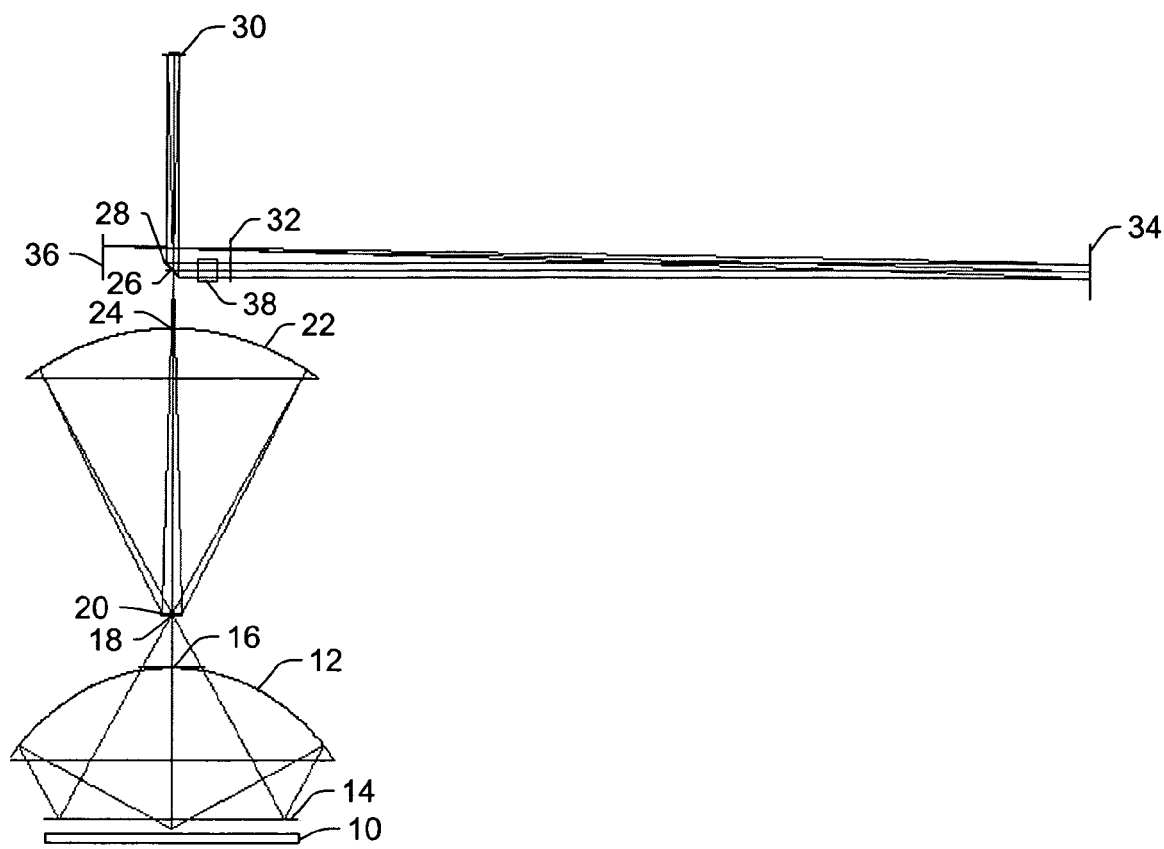
FIG. 1 is a schematic diagram illustrating a cross-sectional view of one embodiment of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defect" generally refers to any abnormality or undesirable feature that may be formed on or within a wafer.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit, a thin-film head die, a micro-electromechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that FIGS. 1 and 3-8 are not drawn to scale. In particular, the scale of some of the elements of the figures is greatly exaggerated to emphasize characteristics of the elements. It is also noted that FIGS. 1 and 3-8 are not drawn to the same scale. Elements shown in more than one figure that may be similarly configured have been indicated using the same reference numerals.

FIG. 1 illustrates one embodiment of a system configured to inspect a wafer. The system includes an optical subsystem. Wafer 10 may be disposed on a stage (not shown), which may be configured to support the wafer, align the rotation of the wafer, focus the wafer at the focal plane of the optical system, and move the wafer with respect to the optical subsystem. The stage may include any suitable mechanical or robotic device known in the art. The optical subsystem is configured to direct specularly reflected, scattered, and diffracted light from wafer 10 to detector 36 such that signals generated by the detector can be used for inspection of the wafer. For instance, light reflected, scattered, diffracted, or otherwise returned from wafer 10 is collected by reflective optical component 12, which in one embodiment may be an asphere. Light collected by reflective optical component 12 is directed to flat reflective optical component 14, which directs the light through aperture 16 of reflective optical component 12.

Although examples of several reflective optical components are described herein as being "flat" or "flat" mirrors, it is to be understood that such reflective optical components may not in reality be perfectly flat. For example, flat reflective optical components described herein may be designed to be substantially or nearly flat. In addition, the "flatness" of the reflective optical components may be determined by manufacturing processes used to fabricate the reflective optical components, which may only be capable of producing reflective optical components that are substantially or nearly, but not perfectly, flat. "Flat" reflective elements can also have higher order aspheric components describing their shape, but have a spherical component that is flat.

Referring back to FIG. 1, light that passes through aperture 16 then passes through aperture 18 of reflective optical component 20, which in one embodiment may be an asphere. Light that passes through aperture 18 is collected by reflective optical component 22, which may also be an asphere. Reflective optical component 22 focuses the light to reflective optical component 20. Light reflected by reflective optical component 20 is directed through aperture 24 of reflective optical component 22. Light that passes through aperture 24 is directed through aperture 26 of reflective optical component 28, which may be a tilted flat reflective optical component. Light that passes through aperture 26 is directed to reflective optical component 30, which may be a parabolic mirror or another mirror having some appropriate curvature.

Reflective optical component 30 substantially collimates the light and directs the substantially collimated light back to reflective optical component 28. The substantially collimated light reflected by reflective optical component 28 is directed through optical component 38 and through pupil 32 to reflective optical component 34. Reflective optical component 34 may in one embodiment be a tilted or off-axis reflective sphere. Reflective optical component 34 is configured to focus the substantially collimated light to detector 36. Detector 36 may include any suitable detector known in the art such as a charge coupled device (CCD) camera, time delay integration (TDI) camera, or array of photo multipliers.

The success of fabricating the lens shown in FIG. 1 is dependent upon the degree of asphereisity of the reflective optical components. However, the departure from the best-fit sphere of the design of the reflective optical components is within the manufacturing capabilities of world-class, optical-fabrication vendors. Another factor in the success of the lens is the manufacturing tolerances for alignment of the mirrors relative to the optical axis in terms of tip, tilt, de-space, and de-center. To make the design easier to fabricate, the prescription may be altered to include either more or fewer mirrors to make the optical power of each element lower. For example, the design shown in FIG. 1 has 5 mirrors, which form a substantially collimated space with relatively low field angles in which refractive beamsplitter element 38 and any other suitable refractive element(s) can be placed as described further herein. However, alternative designs for the reflective system may include 6 or 7 reflective optical components. In addition, the order of the asphere can affect fabrication cost, and a tradeoff may be made between the number of mirrors and the degree of difficulty in manufacturing. Obviously, the prescription of the lens shown in FIG. 1 may vary depending on the factors described above in addition to other variables of the optical subsystem that can affect prescriptions of lenses. Therefore, a suitable prescription for the lens shown in FIG. 1 can be determined by one of ordinary skill in the art based on the description provided herein, and all such suitable prescriptions are within the scope of the embodiments described herein.

The optical subsystem shown in FIG. 1, therefore, provides a substantially collimated space in which system pupil 32 is located. In addition, all refractive optical components are located in substantially collimated space to eliminate aberrations. Such an optical subsystem configuration has many advantages over other optical subsystems. For instance, the optical subsystem can be used for broadband wafer inspection. In particular, the optical subsystem is configured for inspection of the wafer across a waveband of greater than 20 nm. In addition, since the optical subsystem does not include refractive optical components in non-collimated space, the optical subsystem can be used for inspection of the wafer across a waveband of greater than 20 nm that includes wavelengths below and above 200 nm. In this manner, the optical subsystem may be used for broadband wafer inspection at wavelengths that were previously prohibited due to lack of a suitable combination of refractive materials that can be used to correct color aberrations over a broad range of wavelengths.

Figure 2:
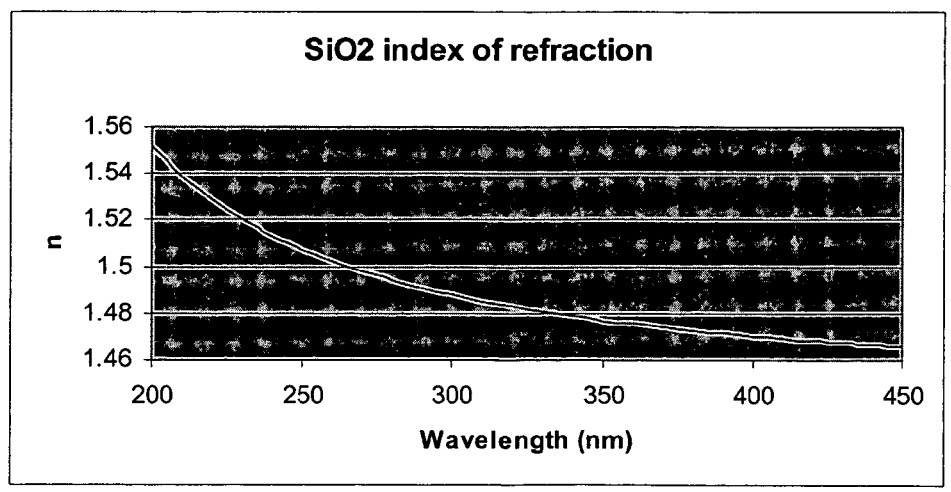
FIG. 2 is a plot illustrating dispersion of fused silica as a function of wavelength.

The broadband inspection systems described herein are, therefore, particularly advantageous over other system configurations that have been attempted in efforts to develop an optical system that is broadband in the wavelengths below 250 nm. For instance, to design a broadband refractive optical system, one needs to have two or more dissimilar optical materials, each having a different dispersion such that the chromatic aberrations of one lens type can be balanced with another at specific design wavelengths. Because the dispersions of fused silica and $CaF_2$ are so similar, the bandwidth obtained in an all refractive lens with just these two materials is usually less than 1 nm for high-numerical aperture requirements. When the two materials are paired with a catadioptric element, then bandwidths of up to 20 nm can be achieved with the lower wavelength around 200 nm. Both of these attempts have been limited by the dispersion of fused silica, which is substantially high at wavelengths below 250 nm, as shown in FIG. 2. Designs using fused silica and calcium fluoride ($CaF_2$), which is the only other refractive material that is production worthy, have not succeeded in achieving wavebands of greater than 20 nm at these wavelengths. In addition, the waveband of such refractive optical systems is not sufficient to allow wavelength optimizing, which involves matching the waveband of the illumination with the defect type and wafer layer structures. For instance, a waveband of greater than about 60 nm is required to perform wavelength optimizing successfully. In addition, as described further in the background section, the transmission of fused silica at wavelengths below about 185 nm is unacceptably low due to absorption of the light of the oxygen molecules in fused silica. Therefore, fused silica may not be usable at all in optical systems designed to operate at wavelengths below about 185 nm.

The systems described herein, therefore, advantageously provide a broadband optical subsystem that can be used for wafer inspection in a bandwidth that can include ultra deep wavelengths at which refractive or catadioptric solutions are not feasible. In particular, since the optical subsystem shown in FIG. 1 does not include any refractive optical components in the non-collimated space, this optical subsystem will not suffer from the chromatic aberration, dispersion, and transmission problems described above. Therefore, the optical subsystem can be used for broadband wafer inspection across a substantially large waveband that includes wavelengths from the vacuum ultraviolet (VUV) regime to the visible regime. For example, the optical subsystem may be configured for inspection of the wafer across a waveband that includes wavelengths in a range from about 150 nm to about 450 nm. In this manner, in some embodiments, the optical subsystem can be configured as a broadband optical subsystem that is configured for inspection of the wafer at wavelengths less than 200 nm. The optical subsystem may also be configured for inspection of the wafer at wavelengths greater than 200 nm.

The optical subsystem may, therefore, be configured to perform wafer inspection across a waveband of 300 nm. However, the waveband that is selected for wafer inspection may vary depending on a number of factors. For instance, the waveband may be selected based on characteristics of the wafer such as defect type(s) and structures formed on the wafer. In one such example, the waveband may be selected based on characteristics such as defect size, defect depth within a structure, structures that are located near the defect, and resonance between the defect and the structures. In addition, the waveband may be selected to include wavelengths for which materials on the wafer are both opaque and transparent. In another example, the waveband may be selected to increase the signal-to-noise ratio corresponding to a defect on the wafer. Increasing the defect signal particularly with respect to the background signal will improve the signal-to-noise ratio of the inspection data thereby enhancing defect detection. In this manner, the waveband can be selected to provide the optimum defect signal. Examples of methods for selecting an appropriate wavelength or wavelengths for wafer inspection are illustrated in commonly assigned U.S. Pat. No. 6,570,650 to Guan et al., which is incorporated by reference as if fully set forth herein. The wavelength(s) of the inspection systems described herein may also be selected as described in this patent.

Therefore, the optical subsystem is configured to operate at a waveband of at least more than 20 nm. However, the waveband across which inspection is performed by the optical subsystem may be 100 nm or more, 300 nm or more, 400 nm or more, and even 500 nm or more. In this manner, the optical subsystems provide wafer inspection across a substantially large bandwidth. Obviously, the efficiency of the reflective coatings on the reflective optical components may determine the useful waveband of the optical subsystem. Therefore, the reflective coatings on the reflective optical components may be selected depending on the design waveband of the system such that the reflection coatings have relatively high efficiency. In some instances, the coatings on the reflective optical components may include one or more layers such as metallic layers and/or dielectric layers. In addition, the coatings on different reflective optical components of the optical subsystem may be different depending on the desired performance of the various reflective optical components.

As further shown in FIG. 1, pupil 32 is not located within an optical component of the optical subsystem. In this manner, pupil 32, which is located in the collection path of the optical subsystem, is accessible. Such a configuration provides significant advantages over other inspection systems. For instance, in many inspection systems, the pupil is located within a lens element of the system or within the objective lens mounting. In this manner, the pupil of such inspection systems is inaccessible. In contrast, since the pupil in the collection path of the system shown in FIG. 1 is accessible, various optical components may be inserted in the path of the collected light at the pupil. In addition, the optical components inserted at the collection pupil may be altered depending on the type of inspection that will be performed and/or the type of wafer that will be inspected.

One or more optical components may be moved into and out of pupil 32 using any methods or devices known in the art.

The optical components that may be located at pupil 32 may include, for example, polarizing components, phase plates, waveband filters, blocking apertures, combinations of these elements, and any other suitable optical components known in the art. In addition, since the pupil is located in substantially collimated space, refractive optical components may be inserted in the pupil without introducing chromatic aberrations to the collected light or altering the dispersion of the collected light. If the optical components inserted in pupil 32 are refractive optical components, the optical components are preferably formed of a material such as $CaF_2$ or another material that has relatively high transmission across the entire waveband of the optical subsystem.

The Fourier plane of the optical subsystem may also be located at pupil 32 in the collection path. In this manner, the optical subsystem may also be configured to have an accessible Fourier plane. As such, the one or more optical components that may be located at pupil 32 may include a Fourier filtering component. The Fourier filtering component may include a spatial filter or another suitable component that can be used to remove light that is reflected and/or scattered by regular patterned features on the wafer from the collection path. By filtering out the collected light that is reflected and/or scattered by repeating features on the wafer, only randomly scattered light will pass through the Fourier filter and on to the detector thereby enhancing defect detection of the system. In addition, in some embodiments, the optical subsystem may be configured such that the Fourier plane obeys the sine law. The sine law generally describes diffraction of light caused by repeating patterns on the surface of the wafer, which cause the light to diffract at approximately uniform angles at regularly spaced intervals. The sine law is defined by the equation: $N\lambda = d\sin(\phi)$, where N is the order of diffraction, $\lambda$ is the wavelength, d is the pitch of the repetitive pattern, and $\phi$ is the diffraction angle.

In addition, since the optical components of the optical subsystem are relatively large with respect to the field of view of the system, as shown in FIG. 1, the optical subsystem is substantially telecentric in object space. Telecentricity of the optical subsystem is advantageous in that light rays incident on the wafer from the illumination are arriving with the same chief ray direction across the field of view indicating that sensitivity will be constant over the field of view. Therefore, the telecentricity of the optical subsystem advantageously increases the simplicity and efficiency of Fourier filtering at the collection pupil.

In alternative embodiments, Fourier filtering may not be performed optically. For instance, non-Fourier filtered light may be directed to the detector, and filtering of signals generated by the detector may be performed by a processor or computer system (not shown) coupled to the detector. The processor or computer system may include any suitable processing component known in the art. In addition, the processor or computer system may be coupled to the detector in any manner known in the art and may be further configured as described herein. Such post-data acquisition Fourier filtering can be performed, for example, as described in commonly assigned U.S. Pat. No. 6,603,541 to Lange, which is incorporated by reference as if fully set forth herein.

In one embodiment, the optical subsystem may include refractive beamsplitter element 38 located in substantially collimated space, as shown in FIG. 1. In one such embodiment, the refractive beamsplitter element may be formed of $CaF_2$ or another refractive material that has relatively high transmission across the entire waveband of the optical subsystem. For example, $CaF_2$ is transparent across wavelengths from about 150 nm to wavelengths in the visible range thereby allowing the optical subsystem to perform wafer inspection across these wavelengths. In another embodiment, the refractive beamsplitter element may be formed of fused silica. Such a refractive beamsplitter element is suitable for operation at a waveband that includes wavelengths greater than about 190 nm. In addition, since the refractive beamsplitter element is located in substantially collimated space, the refractive beamsplitter element will not introduce chromatic or other aberrations to the collected light and will not alter the dispersion of the collected light.

Figure 3:
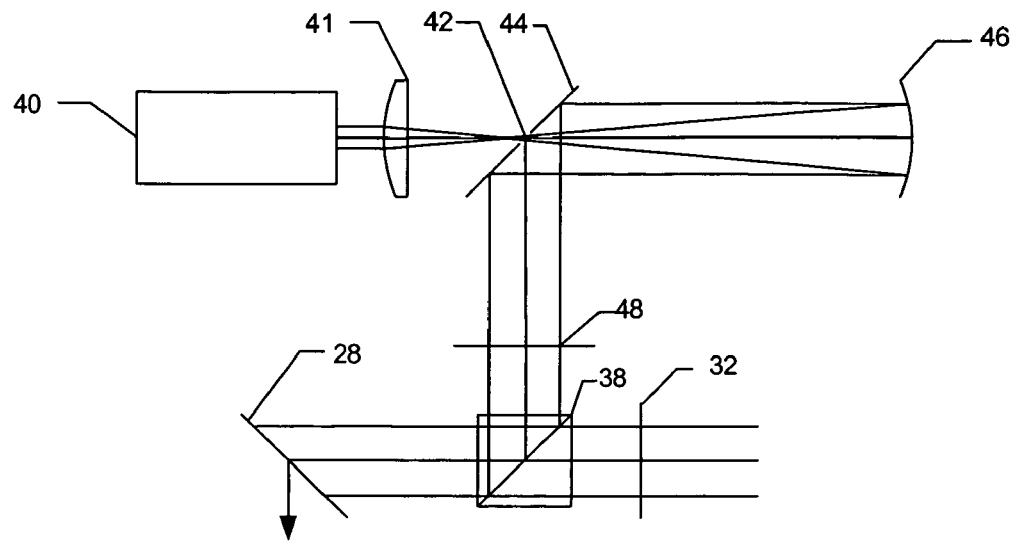
FIGS. 3-4 are schematic diagrams illustrating a cross-sectional view of various embodiments of one or more light sources that can be included in a system configured to inspect a wafer.

Refractive beamsplitter element 38 may be used to couple illumination into the optical subsystem. In addition, the optical subsystem shown in FIG. 1 may include one or more light sources that are used to provide illumination for inspection. One embodiment of a configuration that can be used to couple light from one light source into the optical subsystem is shown in FIG. 3. As shown in FIG. 3, light source 40 is configured to direct light through lens 41 and through aperture 42 in reflective optical component 44, which may be a flat mirror. Light that passes through aperture 42 is directed to reflective optical component 46, which in combination with lens 41 act as a beam expander to fill the aperture of pupil 48. Reflective optical component 46 may be a parabolic mirror or another mirror having some appropriate curvature. Reflective optical component 46 substantially collimates the light and directs the substantially collimated light back to tilted reflective optical component 44.

Reflective optical component 44 directs the substantially collimated light to beamsplitter 38, which may be positioned in the optical subsystem as shown in FIG. 1. In this manner, the refractive beamsplitter element is also located in substantially collimated space in the illumination path. Therefore, the beamsplitter element will not introduce chromatic or other aberrations in the illumination and will not alter the dispersion of the illumination. Illumination directed to refractive beamsplitter element 38 is directed by the beamsplitter to reflective optical component 28 and is then directed by the reflective optical components described above to wafer 10. Therefore, illumination reflected by refractive beamsplitter element 38 may travel along the same optical path as the collected light but in the opposite direction. In this manner, as shown in FIG. 1, the optical subsystem may direct light to the wafer at a high numerical aperture (NA). For example, the NA on the object side of the optical subsystem may be greater than about 0.70. In another example, the NA on the object side of the optical subsystem may be greater than or equal to about 0.90.

As shown in FIG. 3, pupil 48 of the optical subsystem located in the illumination path is not located within an optical component and is located at an equal distance from beamsplitter 38 as collection pupil 32 from beamsplitter 38. In this manner, the pupil in the illumination path, like the pupil in the collection path, is accessible. As such, various optical components may be located at the illumination pupil such as beam shaping components, wavelength selecting filters, phase altering components, attenuating filters, blocking apertures, polarizing components, any other appropriate optical components known in the art, and some combination thereof. In addition, since the illumination pupil is located in the substantially collimated space, the optical components located at the pupil in the illumination path may include refractive optical components, which may be configured as described further above.

Furthermore, pupil 48 in the illumination path is separated from pupil 32 in the collection path. The pupil is separated in the illumination and collection paths by beamsplitter 38. Therefore, the optical subsystem is configured to have an accessible pupil that is separated in the illumination and collection paths. Such separation of the pupil provides increased flexibility in that different optical components may be located at the pupils in the illumination and collection paths. For example, different polarizing components may be positioned at the pupils in the illumination and collection paths. In another example, a wavelength selecting filter may be positioned at the pupil in the illumination path, and a Fourier filter may be placed at the pupil in the collection path. In a further example, blocking apertures may be positioned at the pupils in the illumination and collection paths. The blocking apertures may be configured to manipulate the shapes of the pupils such that inspection in various brightfield and darkfield modes may be performed. Other optical components that alter the polarization and/or phase of the light can be inserted in the illumination and/or collection pupil to maximize the signal-to-noise ratio of wafer defects. Many other such combinations are possible, and all such combinations are within the scope of the embodiments described herein.

Figure 4:
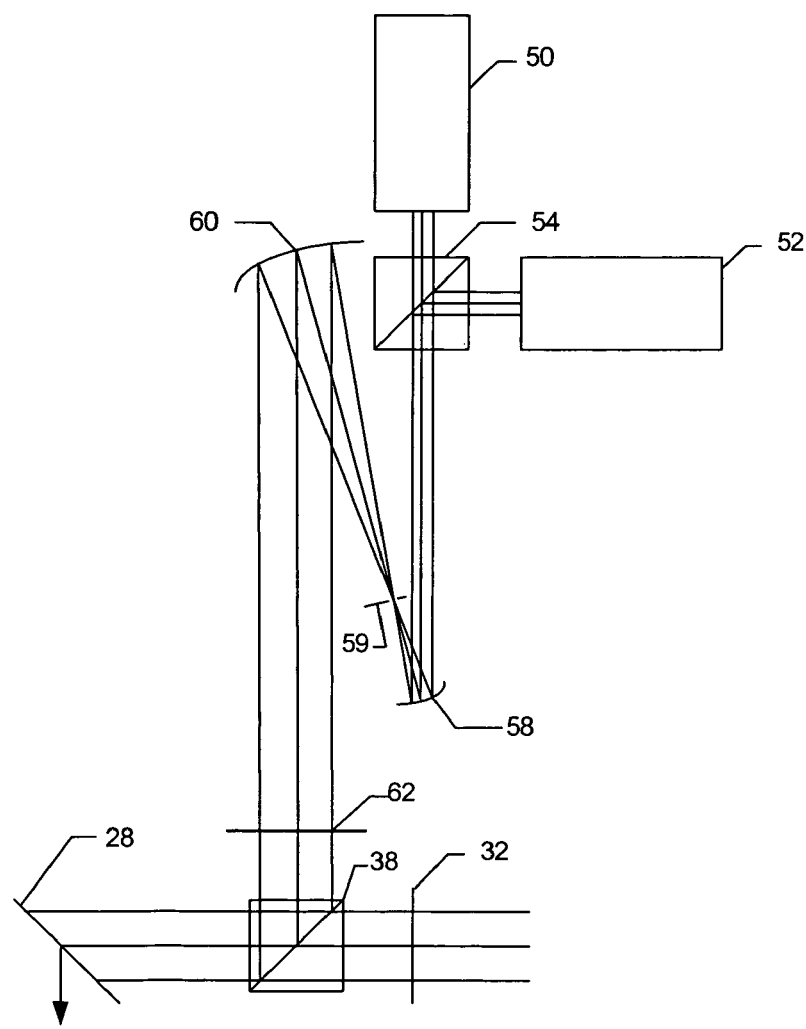

One embodiment of a configuration that can be used to couple light from more than one light source into the optical subsystem is shown in FIG. 4. As shown in FIG. 4, light from light sources 50 and 52 is directed to optical component 54. Optical component 54 is preferably a refractive dichroic beamsplitter since it is located in collimated space. In this manner, optical component 54 will not introduce chromatic or other aberrations to the illumination. Refractive optical component 54 may include a dichroic beamsplitter which can pass light from source 50 through it and reflect light from source 52 toward beam expander element 58. In some embodiments, the two light beams from light sources 50 and 52 may have substantially the same LaGrange Invariant at reflective optical component 54 such that the light from the two light sources has approximately the same distribution of light (e.g., size and angular extent). In this manner, the two light beams may be properly joined into a single light beam. As such, the combined light beams may be directed to the wafer at the same time for inspection.

Reflective optical component 60, which may be an off-axis paraboloid, is configured to substantially collimate the light and to direct the substantially collimated light back to pupil 62 and then to refractive beamsplitter element 38, which may be positioned in the optical subsystem as shown in FIG. 1. Field stop 59 is located between mirror 58 and mirror 60, which is conjugate to the wafer plane. This embodiment of the illumination portion of the optical subsystem also has pupil 62, which is located in substantially collimated space and is separate from the pupil in the collection path. Therefore, an optical subsystem including the light sources and optical components shown in FIG. 4 will also have the advantages of separate and accessible pupils as described above.

Although two different configurations are shown in FIGS. 3 and 4 for coupling light from one or more light sources into the optical subsystem, it is to be understood that many suitable optical configurations are possible, and all such variations are within the scope of the embodiments described herein. For example, combining sources having different wavelengths can be accomplished using a dichroic beamsplitter positioned in substantially collimated space. In addition, although the configuration shown in FIG. 4 can be used to direct multiple light beams to a wafer simultaneously, this configuration may also be used to sequentially direct light from the light sources to the wafer. In addition, the configuration shown in FIG. 4 can be modified to couple light from more than two light sources into the optical subsystem. Furthermore, additional illumination optical elements may be used to create a field stop conjugate to the wafer surface or to homogenize the spatial uniformity of the illumination beams in a manner consistent with the utilization of all reflective components or refractive components operating in a manner to not introduce chromatic aberrations.

Furthermore, the optical illumination subsystem may be configured such that a beam of light may be directed to the wafer at an oblique angle of incidence. One method for directing light to the wafer at an oblique angle of incidence is to direct the light to the wafer through a space located between the upper surface of the wafer and the bottom surface of reflective optical component 14. In this manner, light may be directed to the wafer through space external to the lens of the optical subsystem and not having to reflect off any optical surface in the imaging path. In another example, light may be directed to the wafer at an oblique angle of incidence through a relatively small off-center aperture in reflective optical component 12. Light resulting from oblique illumination of the wafer may be collected and detected as described herein.

In another embodiment, the light from the source may be sent directly to the wafer through a hole (not shown) in reflective optical component 14 either by using the space between reflective optical components 12 and 14 or by having one or more holes (e.g., different holes for various elevation and azimuth angles of incidence) in reflective optical component 12. For such embodiments, the collection optics may be configured as described herein possibly with the collection pupil acting as a Fourier filter.

The light source(s) shown in FIGS. 3 and 4 may include a number of different sources. Preferably, the light source(s) include at least one broadband source or a source containing a number of simultaneous narrow bands. In addition, broadband source(s) that have relatively high brightness may be particularly suitable for inclusion in the optical subsystem. One embodiment of a light source that may be included in the optical subsystem is a cascade arc, which has a high blackbody temperatures in excess of 10,000K, and which produces relatively large amounts of deep ultraviolet (DUV) light in a semi-coherent manner. In addition, the cascade arc provides light across an extensive waveband from below about 150 nm to above about 450 nm. The optical subsystem may also include arc lamps (e.g., mercury-xenon (HgXe) arc lamps) for illumination above 230 nm and lasers for individual wavelengths.

Possible laser sources include frequency doubled or mixed YAG lasers that produce light at wavelengths of 532 nm, 355 nm, and 266 nm, argon ion lasers that produce light at 257 nm, frequency doubled argon ion lasers that produce light at 244 nm, excimer lasers that produce light at 157 nm, 193 nm, or 248 nm, frequency mixed lasers that produce light at 198 nm or 193 nm, and optically pumped atomic vapor lasers that produce light at 185 nm (Hg) and 222 nm (cesium, Cs) with others in the waveband of about 140 nm to about 450 nm. In addition, the laser may be a continuous (CW) laser or a pulsed laser, preferably having a relatively long pulse duration. The laser may also include a laser that is configured to generate light at some harmonic. For instance, a laser that emits light at the 8th harmonic may be used. Light generated at lower harmonics of such a laser (e.g., 7th, 6th, 5th, etc.) may also be used for illumination either simultaneously, individually, or in any combination. In this manner, the optical subsystem may be configured to direct light at one of the multiple harmonics to the wafer, light at a plurality of the multiple harmonics to the wafer sequentially, or light at a plurality of the multiple harmonics to the wafer simultaneously. Such lasers that may be suitable for use in the optical subsystems described herein are currently being developed for commercial applications by companies such as Nikon Corporation. If Fourier filtering of the collected light is to be performed as described above, it may be advantageous to use a coherent light source for illumination.

Any of the above light sources may be used singly or in any combination thereof. For instance, in one embodiment, the one or more light sources include one or more fiber lasers. In other embodiments, the one or more light sources include an arc lamp, a laser, a laser configured to generate light at multiple harmonics, or some combination thereof.

The high-brightness light source used in the optical subsystem preferably matches the etendue of the illumination numerical aperture (NA) and field of view (FOV). Etendue can be generally defined as the size of the image on the image plane times the angle at which the image travels from the lens to the image plane. Therefore, etendue is generally a measure of brightness of the image. In general, a relatively small etendue is preferable such that a relatively small image can be formed on the object plane at relatively high NA. Etendue matching may be accomplished, for example, with a separate zoom on the illumination if the illumination source has enough brightness, which may or may not equal the etendue of the detector through its zoom range. A zoom used for illumination may be configured as described herein. The etendue of the illumination and collection may not be equal if sigma of the optical subsystem does not equal 1 and for various darkfield (DF) inspection options. Sigma can be generally defined as a ratio of the illumination NA of the optical subsystem to the collection NA of the optical subsystem.

Figure 5:
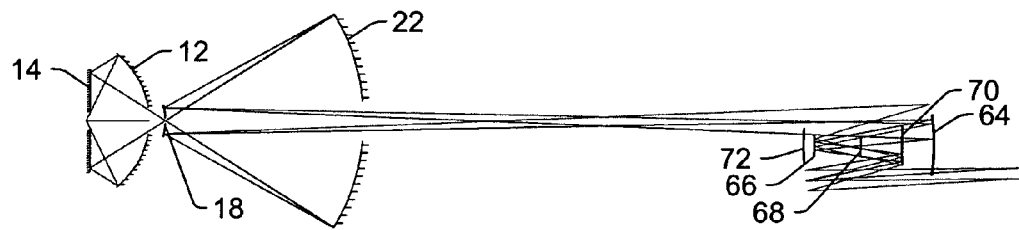
FIG. 5 is a schematic diagram illustrating a cross-sectional view of another embodiment of a system configured to inspect a wafer.

A different embodiment of a system that is configured to inspect a wafer is shown in FIG. 5. This system also includes an optical subsystem, which includes only reflective light-directing optical components in non-collimated space. For example, the optical subsystem shown in FIG. 5 includes reflective optical components 12, 14, 18, and 22, which may be configured as described above with respect to the reflective optical components with like reference numerals shown in FIG. 1.

However, the system shown in FIG. 5 has a set of reflective optical components that is configured to substantially collimate the light reflected by reflective optical component 18 and to direct the substantially collimated light through a pupil of the collection path to a zoom subsystem. In particular, as shown in FIG. 5, reflective optical component 64, which may be a spherical mirror or another mirror having some appropriate curvature, is configured to substantially collimate the light reflected by reflective optical component 18. The substantially collimated light is directed to reflective optical component 66, which directs the light through pupil 68 of the collection path. In this manner, pupil 68 is located in substantially collimated space.

Light that passes through the pupil is directed to reflective optical component 70, which may also be a flat or spherical mirror. In addition, although pupil 68 is disposed between two reflective optical components that are much closer than those between which the collection pupil of FIG. 1 is disposed, pupil 68 is still readily accessible. Therefore, one or more optical components may be located at pupil 68. These optical component(s) may include any of those described above and may be moved into and out of the collection pupil depending on the type of inspection that will be performed and/or the characteristics of the wafer that will be inspected. Light reflected by reflective optical component 70 is directed to reflective optical component 72, which may be a spherical mirror or another mirror having some appropriate curvature. Reflective optical component 72 directs the light to a zoom subsystem (not shown in FIG. 5), which may be configured as described further herein. The system shown in FIG. 5 may be further configured as described herein. All of these mirrors 64, 70, 66, and 72 can be segments of round mirrors so as to not interfere or block the light path. The prescription for all of these mirrors can be altered to perform the same function, which is to provide a substantially collimated space for the beamsplitter with enough room for optical elements in the pupil.

The reflective optical components shown in FIG. 1 include two optical components that are configured to alter a magnification or the "zoom" of light collected by the optical subsystem. In this manner, the system preferably includes an all-reflective zoom. As such, the zoom subsystem will not introduce chromatic and other aberrations in the light even when the magnification of the optical subsystem is changed. For instance, in the embodiment shown in FIG. 1, reflective optical components 30 and 34 may be used to control the magnification of the optical subsystem over a limited range. The magnification may be altered by altering a position of reflective optical components 30 and 34. The position of these reflective components may be altered using any appropriate components (not shown) known in the art such as mechanical components that are coupled to the reflective optical components and can be controlled by a processor or computer system. The optical subsystem may be configured as a relatively high magnification system. For instance, in one embodiment, the optical subsystem may be configured to have a magnification from about 50× to about 500×.

As shown in FIG. 1, therefore, the zoom of the optical subsystem includes two reflective optical components. However, the zoom subsystem included in the optical subsystem shown in FIG. 1 may include two or more optical components that are configured to alter a magnification of light collected by the optical subsystem. In this manner, the zoom of the optical subsystem may be controlled by more than two reflective optical components. Using more than two reflective optical components to control the magnification of the optical subsystem may provide better image quality over the magnification range.

Figure 6:
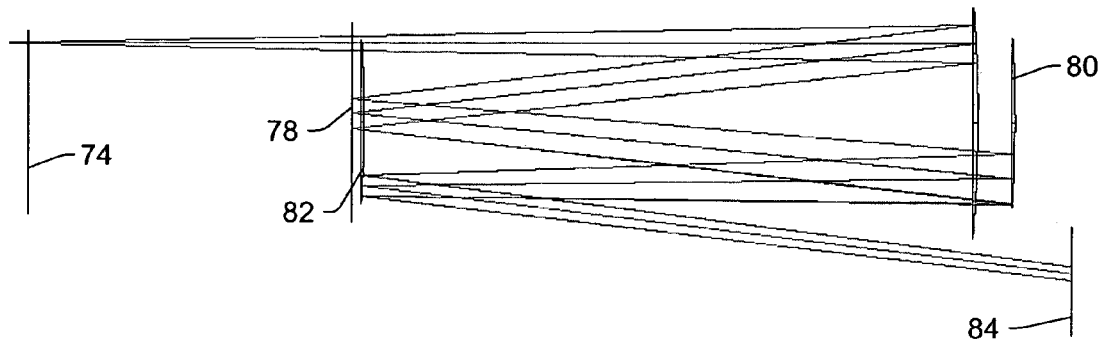
FIGS. 6-8 are schematic diagrams illustrating a cross-sectional view of different embodiments of reflective optical components configured to alter a magnification of light collected by an optical subsystem.

One embodiment of reflective optical components that are configured to alter a magnification of light collected by the optical subsystem is illustrated in FIG. 6. In the embodiment shown in FIG. 6, the zoom subsystem includes four reflective spherical optical components. In particular, light that passes through field stop 74 is directed to reflective optical component 76, which in one example may be a mirror having some curvature. Light reflected by reflective optical component 76 is directed to reflective optical component 78, which in this example is a spherical mirror. Light reflected from reflective optical component 78 is directed to reflective optical component 80, which may be a mirror having some curvature. Light reflected by reflective optical component 80 is directed to reflective optical component 82, which may also be a mirror having some curvature. Light reflected by reflective optical component 82 is directed to image plane 84. Mirrors 76, 78, 80, and 82 may be segments of circular elements to avoid blocking the light beam.

To alter the magnification of the optical subsystem, the set of four reflective optical components 76, 78, 80, and 82 may be moved linearly toward and away from the field stop. A minimum distance between the field stop and reflective optical component 78 may be about 53 mm. In addition, the overall length of the set of four reflective optical components may be about 130 mm. The overall width of the set of four reflective optical components may be about 42 mm. The zoom subsystem shown in FIG. 6 may be included in any of the system embodiments described herein.

Figure 7:
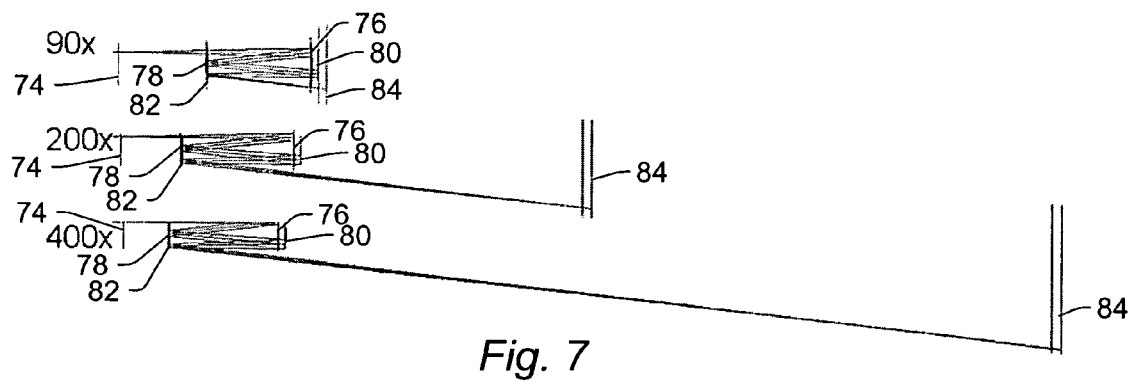

The configuration of the zooming reflective elements may be varied depending on the magnification selected for the optical subsystem. However, the general configuration of four reflective components used for zooming shown in FIG. 6 may be used for a variety of magnifications. For example, as shown in FIG. 7, a four reflective component zoom subsystem may be used to provide a magnification of about 90×, about 200×, or about 400× for the optical subsystem. The configuration of one or more of the reflective zooming elements may be varied depending on the selected magnification. In addition, the positions of the reflective zooming elements with respect to one another may be varied depending on the selected magnification. In this manner, a zooming subsystem that includes two or more reflective optical components may be used for one selected magnification.

Figure 8:
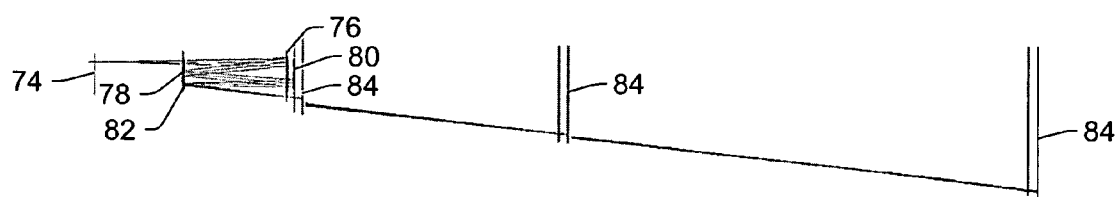

However, the four reflective component zoom subsystem may be used to provide a variety of magnifications, as shown in FIG. 8. In particular, the positions of the reflective zooming components may be varied by both tilting and linear motion to provide different magnifications such as those described above. The overall length of the optical path of the zooming element configuration may be approximately 795 mm. The zoom subsystem configurations shown in FIGS. 6-8 may be included in any of the system embodiments described herein.

The systems described herein have a number of advantages in addition to those described above. For example, in one embodiment, the optical subsystem is configured to have a low central obscuration. Obscuration can be generally defined by a ratio of the size of an aperture formed through a reflective optical component versus the size of the reflective optical component. The obscuration is preferably as low as possible, and the obscuration of the optical subsystem is limited by the reflective optical component having the highest obscuration ratio. As shown in FIG. 1, all of the reflective optical components of the optical subsystem have a relatively low obscuration ratio. In particular, for each reflective optical component having an aperture formed therein, the size of each reflective optical component is relatively large in comparison to the size of its aperture. Therefore, the optical subsystem as a whole will have a relatively low obscuration.

In another embodiment, the NA on the object side of the optical subsystem is greater than about 0.70. In a preferred embodiment, the NA on the object side of the optical subsystem is greater than or equal to about 0.90. In additional embodiment, a field of view of the optical subsystem is greater than about 0.1 mm. In some embodiments, the field of view (FOV) of the optical subsystem is greater than or equal to about 0.8 mm. In this manner, the optical subsystem may have a relatively large FOV compared to other wafer inspection systems. In a further embodiment, the optical subsystem is low in distortion. Distortion can be generally defined as errors in the location of the collected light at the detector. The low distortion of the optical subsystem may be due at least in part to the telecentricity of the optical subsystem. In this manner, the optical subsystem may have substantially good image quality, which may at least in part facilitate highly accurate defect detection.

The optical subsystems described herein, therefore, can be used for high-end line monitor (HELM) wafer inspection since the optical subsystems described herein meet all of the specifications for such inspection. In particular, specifications for HELM wafer inspection include a relatively large NA (e.g., 0.90 or greater), relatively large FOV (e.g., 0.8 mm), telecentricity in object space, low distortion, an accessible pupil that can be separated between illumination and collections paths, a high magnification potential, a zoomable magnification, and a substantially collimated space where a beamsplitter can be inserted without introducing aberrations. The systems described herein meet these specifications in addition to providing the capability for a broad waveband through the use of all reflective optical elements in non-collimated space. Furthermore, the optical subsystems described herein have relatively good resolution due at least in part to the substantially low wavelengths at which the optical subsystems can operate. Resolution tends to be equal to the wavelength of the system divided by the NA of the system. In addition, the optical subsystem can be used for a variety of inspection modes includes brightfield (BF), DF, imaging, non-imaging, etc.

The sensitivity requirements for inspection parallel the sensitivity of the lithography roadmap. Options for meeting these sensitivity requirements, other than those provided by the embodiments described herein, include immersion lenses, which can increase the resolution of an inspection system by the ratio of the index of refraction of the immersion liquid, typically water with an index of about 1.43 in the DUV waveband. However, the applicability of immersion lenses to wafer inspection is significantly reduced due to the similarity of the immersion liquid's index of refraction compared to the index of refraction for many wafer materials (e.g., oxides and photoresists) thereby yielding little image contrast.

With sensitivity for other systems already not equaling market requirements, there is a need to further increase sensitivity with wavelength scaling, particularly in the BF arena. The systems described herein provide the desired sensitivity since the wavelengths used for inspection can be dramatically lower than other inspection systems. For instance, the systems described herein can be used at the 32 nm lithographic production node. In addition, the reflective designs described herein allows significant bandwidth such that material contrast properties can be spanned with wavelengths below and above absorption edges. The designs described herein also provides for wavelength band selectivity such that the waveband can be chosen to optimize sensitivity for a particular defect on a particular defect layer.

As described above, the optical subsystem embodiments described herein can be used for broadband wafer inspection applications at wavelengths below 200 nm (as well as wavelengths above 200 nm). As known in the art, at wavelengths below 185 nm, light may be partially or totally absorbed by water, oxygen, and air that are present in the optical path of an optical system. Therefore, as the wavelength of optical subsystems falls below 190 nm, absorption of the light by water, oxygen, and air can cause significant problems for these systems. As such, in one embodiment, the optical subsystems described herein may be disposed in a purged environment during inspection (e.g., using a gas that is substantially transparent at the wavelengths). Examples of methods and systems for generating a purged environment for an optical subsystem are illustrated in co-pending, commonly assigned U.S. patent application Ser. No. 10/846,053 to Fielden et al. filed May 14, 2004, which is incorporated by reference as if fully set forth herein.

The systems described herein may also include a processor or computer system (not shown) as described above. The processor or computer system may be configured to detect defects in the signals generated by detector 36 shown in FIG. 1. The processor or computer system may be configured to use any method or algorithm known in the art for defect detection. In some embodiments, the processor or computer system may also be configured to perform review of the defects on the wafer using the signals generated by detector 36. In this manner, the systems described herein may be configured for inspection and review of defects on a wafer. The processor may also be configured to perform other defect-related functions such as defect classification. The processor or computer system may include any appropriate processor or computer system known in the art.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool" or a number of process modules coupled by a common handler.

The results of the inspection and/or review performed by the systems described herein may be used to alter a parameter of a process or a process tool using a feedback control technique, a feedforward control technique, or an in situ control technique. The parameter of the process or the process tool may be altered manually or automatically.

Another embodiment relates to a method for inspecting a wafer. The method includes directing light from a light source to the wafer through non-collimated space using only reflective optical components. Directing the light from the light source to the wafer may be performed using any of the system embodiments described herein. For instance, light from light source 40 shown in FIG. 2 may be directed to wafer 10 shown in FIG. 1 using reflective optical components 20, 22, 14, and 12, which are located in non-collimated space as shown in FIG. 1. Reflective optical components may also be used to direct the light in substantially collimated space as well as described further herein.

The light has a waveband of greater than 20 nm. The waveband, however, may include any of the wavebands described above. In addition, the waveband may include any of the wavelengths described above (e.g., from below 150 nm to above about 450 nm). In one embodiment, the method may include selecting the waveband based on characteristics of the wafer. In another embodiment, the method may include selecting the waveband to include wavelengths at which materials on the wafer are both opaque and transparent. In some embodiments, the method may include selecting the waveband to increase the signal-to-noise ratio corresponding to a defect on the wafer. In additional embodiments, the method may include directing light from multiple light sources to the wafer through non-collimated space using only reflective optical components, which may be performed as described above.

In one embodiment, the light from the light source has one or more discrete wavelengths. In one such embodiment, directing the light from the light source to the wafer includes directing light having a single of the one or more discrete wavelengths to the wafer. In a different such embodiment, directing the light from the light source to the wafer includes directing light having a combination of the one or more discrete wavelengths simultaneously to the wafer. Each of the one or more discrete wavelengths may alternatively be directed from the light source to the wafer sequentially.

The method also includes directing light from the wafer to a detector through non-collimated space using only reflective optical components. For instance, light from wafer 10 shown in FIG. 1 may be directed to detector 36 using reflective optical components 12, 14, 22, 20, and 30 in non-collimated space. In one embodiment, the method may include magnifying light collected from the wafer. In some embodiments, the method may include Fourier filtering of light collected from the wafer. Magnification and Fourier filtering may be performed as described above.

In addition, the method includes detecting defects on the wafer using signals generated by the detector. For example, signals generated by detector 36 shown in FIG. 1 may be used by a processor or computer system (not shown) to detect defects on wafer 10. As described above, Fourier filtering may be performed before the collected light is detected. In an alternative embodiment, Fourier filtering may be performed on the signals generated by the detector. Each of the embodiments of the method described above may include any other step(s) described herein. In addition, each of the embodiments of the method described above may be performed using any of the system embodiments described herein.

Further modifications and alternative embodiments of various aspects of the invention may be apparent to those skilled in the art in view of this description. For example, all-reflective optical systems for broadband wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising an optical subsystem, wherein all light-directing optical components of the optical subsystem are reflective optical components except for one or more refractive optical components located only in substantially collimated space, wherein the optical subsystem is configured for inspection of the wafer across a waveband of greater than 20 nm, and wherein a numerical aperture on the object side of the optical subsystem is greater than about 0.70.

2. The system of claim 1, wherein the waveband comprises wavelengths below 200 nm.

3. The system of claim 1, wherein the waveband is selected based on characteristics of the wafer.

4. The system of claim 1, wherein the waveband is selected to comprise wavelengths at which materials on the wafer are both opaque and transparent.

5. The system of claim 1, wherein the waveband is selected to increase a signal-to-noise ratio corresponding to a defect on the wafer.

6. The system of claim 1, wherein the waveband comprises wavelengths in a range from about 150 nm to about 450 nm.

7. The system of claim 1, wherein the optical subsystem comprises one or more light sources.

8. The system of claim 7, wherein the one or more light sources comprise one or more fiber lasers.

9. The system of claim 7, wherein the one or more light sources comprise a laser configured to generate light at multiple harmonics, and wherein the optical subsystem is further configured to direct light at one of the multiple harmonics to the wafer, light at a plurality of the multiple harmonics to the wafer sequentially, or light at a plurality of the multiple harmonics to the wafer simultaneously.

10. The system of claim 7, wherein the one or more light sources comprise a cascade arc.

11. The system of claim 7, wherein the one or more light sources comprise an arc lamp, a laser, a laser configured to generate light at multiple harmonics, or some combination thereof.

12. The system of claim 1, wherein the reflective optical components comprise two or more optical components configured to alter a magnification of light collected by the optical subsystem.

13. The system of claim 1, wherein the optical subsystem is further configured to have a magnification from about 50× to about 500×.

14. The system of claim 1, wherein the optical subsystem is further configured to have a low central obscuration.

15. The system of claim 1, wherein the optical subsystem is further configured to have an accessible pupil separated in illumination and collection paths by a beamsplitter.

16. The system of claim 1, wherein the optical subsystem is further configured to have an accessible Fourier plane.

17. The system of claim 1, wherein the one or more refractive optical components comprise a refractive beamsplitter element located in the substantially collimated space, and wherein the refractive beamsplitter element is formed of calcium fluoride.

18. The system of claim 1, wherein the one or more refractive optical components comprise a refractive beamsplitter element located in the substantially collimated space, wherein the refractive beamsplitter element is formed of fused silica, and wherein the waveband comprises wavelengths greater than about 190 nm.

19. The system of claim 1, wherein the numerical aperture on the object side of the optical subsystem is greater than or equal to about 0.90.

20. The system of claim 1, wherein a field of view of the optical subsystem is greater than about 0.1 mm.

21. The system of claim 1, wherein a field of view of the optical subsystem is greater than or equal to about 0.8 mm.

22. The system of claim 1, wherein the optical subsystem is substantially telecentric in object space.

23. The system of claim 1, wherein the optical subsystem is low in distortion.

24. A system configured to inspect a wafer, comprising a broadband optical subsystem, wherein all light-directing optical components of the broadband optical subsystem are reflective optical components except for one or more refractive optical components located only in substantially collimated space, wherein the broadband optical subsystem is configured for inspection of the wafer at wavelengths both less than and greater than 200 nm, and wherein a numerical aperture on the object side of the optical subsystem is greater than about 0.70.

25. A method for inspecting a wafer, comprising:
directing light from a light source to the wafer through non-collimated space using only reflective optical components, wherein the light has a waveband of greater than 20 nm, wherein the reflective optical components are included in an optical subsystem, and wherein a numerical aperture on the object side of the optical subsystem is greater than about 0.70;
directing light from the wafer to a detector through non-collimated space using only reflective optical components; and
detecting defects on the wafer using signals generated by the detector.

26. The method of claim 25, wherein the light from the light source has one or more discrete wavelengths, and wherein said directing the light from the light source to the wafer comprises directing light having a single of the one or more discrete wavelengths to the wafer.

27. The method of claim 25, wherein the light from the light source has two or more discrete wavelengths, and wherein said directing the light from the light source to the wafer comprises directing light having a combination of the two or more discrete wavelengths simultaneously to the wafer.

* * * * *